United States Patent
Asai et al.

(10) Patent No.: US 7,775,485 B2
(45) Date of Patent: Aug. 17, 2010

(54) DISPLAY SUPPORT ARM AND ULTRASONIC IMAGING APPARATUS

(75) Inventors: Akimasa Asai, Tokyo (JP); Koyoshi Matsumura, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 409 days.

(21) Appl. No.: 11/952,894

(22) Filed: Dec. 7, 2007

(65) Prior Publication Data

US 2008/0132786 A1 Jun. 5, 2008

(30) Foreign Application Priority Data

Dec. 11, 2006 (JP) .............................. 2006-333464

(51) Int. Cl.
*A47F 5/00* (2006.01)
(52) U.S. Cl. ..................... 248/125.7; 248/425; 248/921; 600/437
(58) Field of Classification Search .............. 248/276.1, 248/921, 122.1, 125.7, 425; 600/437
See application file for complete search history.

(56) References Cited

U.S. PATENT DOCUMENTS

| | | | | |
|---|---|---|---|---|
| 4,625,731 | A | * | 12/1986 | Quedens et al. ............. 600/443 |
| 4,687,167 | A | * | 8/1987 | Skalka et al. ................ 248/126 |
| 6,669,639 | B1 | | 12/2003 | Miller et al. |
| D512,508 | S | | 12/2005 | Mesaros |
| D529,611 | S | | 10/2006 | Gumisawa et al. |
| 2003/0001056 | A1 | * | 1/2003 | Ihalainen et al. ......... 248/276.1 |
| 2004/0068185 | A1 | * | 4/2004 | Marshall et al. ............. 600/437 |
| 2008/0228071 | A1 | * | 9/2008 | Mesaros ...................... 600/437 |
| 2008/0234577 | A1 | * | 9/2008 | Murkowski et al. ......... 600/437 |

FOREIGN PATENT DOCUMENTS

| | | |
|---|---|---|
| JP | 2004-344636 | 12/2004 |
| WO | 2005/074806 A | 8/2005 |

\* cited by examiner

*Primary Examiner*—J. Allen Shriver, II
*Assistant Examiner*—Bradley H Duckworth
(74) *Attorney, Agent, or Firm*—Armstrong Teasdale LLP

(57) ABSTRACT

A display support arm includes a first swing arm having a first end portion positioned vertically on top of a housing and further having a second end portion, the first swing arm causing the second end portion to rotate in a horizontal plane with the first end portion as a rotational center, a second swing arm having a third end portion joined vertically to the second end portion and further having a fourth end portion, the second swing arm causing the fourth end portion to rotate in a horizontal plane with the third end potion as a rotational center, a display joined vertically to the fourth end portion, a first lock device for locking a rotational motion of the first swing arm automatically when the housing and the first swing arm reach a predetermined relative position, a second lock device for locking a relative rotational motion of the first and second swing arms automatically when the first and second swing arms vertically reach a position where the two overlap each other, and a lock setting device for switching the first and second lock devices in one behavior to a lockable state able to effect locking automatically in the predetermined relative position and the overlapping position or an unlockable state failing to perform the locking in the predetermined relative position and the overlapping position.

19 Claims, 11 Drawing Sheets

(A)

(B)

(C)

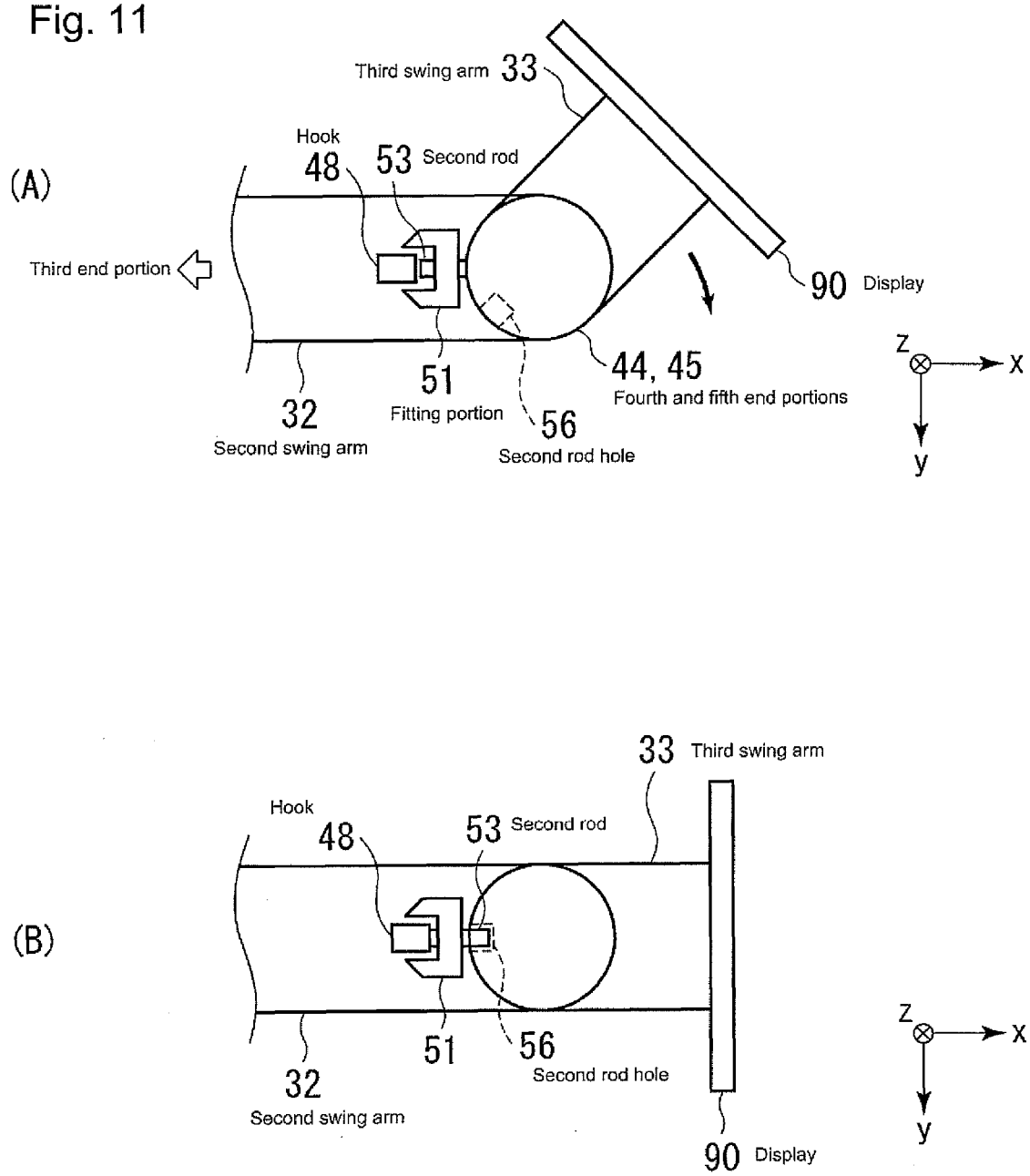

DISPLAY SUPPORT ARM AND ULTRASONIC IMAGING APPARATUS

CROSS REFERENCE TO RELATED APPLICATIONS

This application claims the benefit of Japanese Patent Application No. 2006-333464 filed Dec. 11, 2006.

BACKGROUND OF THE INVENTION

The present invention relates to a display support arm and an ultrasonic imaging apparatus adapted to move within a hospital as necessary and acquire an image at a position, for example, at a bedside position close to a subject.

Recently, the ultrasonic imaging apparatus have widely spread as an apparatus for obtaining a tomographic image of a subject in real time. The ultrasonic imaging apparatus including a display, a body and a probe portion as an integral structure is relatively small-sized and can be moves easily through wheels mounted to a lower portion of the body.

The ultrasonic imaging apparatus can be moved easily by manual pushing of an operator up to a place best suited for acquiring an image of a subject. In this movement is included, for example, a movement between upper and lower floors with use of an elevator installed within a hospital. As the case may be, movement using an automobile or the like is also included.

On the other hand, the display of the ultrasonic imaging apparatus is shifting from CRT (Cathode Ray Tube) to LCD (Liquid Crystal Display) and thus the display is being reduced in weight. With this reduction in weight, it has become possible to dispose the display on top of the body through plural swing arms (see, for example, Patent Literature 1). These swing arms make the display movable in the horizontal direction and the display can be moved to a position somewhat away from the body and which the operator desires. Consequently, in such a narrow area as a bedside area in which the movement of the body is not easy, it is possible to move only the display and the probe portion to near the subject and perform an ultrasonic inspection. This is convenient both subject and operator.

However, the display put on swing arms may undergo a large positional deviation due to vibration or shaking caused by movement of the ultrasonic imaging apparatus. This positional deviation which occurs during movement of the ultrasonic imaging apparatus is likely to cause collision of the display with a wall surface or a passer-by and thus involves a dangerous factor. Therefore, a lock mechanism for fixing the display to ensure safety is provided for the swing arms.

[Patent Literature 1] Japanese Unexamined Patent Publication No. 2004-344636 (pp. 5-6, FIG. 4).

According to the above background art, however, setting the lock mechanism is troublesome, requiring much time and labor. That is, for fixing the display positively to the body of the ultrasonic imaging apparatus, it is necessary that the plural swing arms for carrying the plural swing arms thereon be locked and fixed each individually.

Particularly, when the ultrasonic imaging apparatus is used at a bedside position in a hospital, the apparatus is moved frequently. Locking the plural swing arms carrying the display thereon, which is performed at every such movement, is troublesome. Besides, at a site where an ultrasonic imaging operation is performed, the lock mechanism must not obstruct a free movement of the swing arms from the standpoint of operating performance on the operator side.

Thus, it is important how such display support arm and ultrasonic imaging apparatus as can lock and fix the movement of plural swing arms carrying the display thereon are to be implemented without requiring much time and labor.

SUMMARY OF THE INVENTION

It is desirable that the problem described previously is solved.

In a first aspect of the invention there is provided a display support arm comprising a first swing arm having a first end portion positioned vertically on top of a housing and further having a second end portion, the first swing arm causing the second end portion to rotate in a horizontal plane with the first end portion as a rotational center, a second swing arm having a third end portion joined vertically to the second end portion and further having a fourth end portion, the second swing arm causing the fourth end portion to rotate in a horizontal plane with the third end portion as a rotational center, a display joined vertically to the fourth end portion, a first lock device for locking a rotational motion of the first swing arm automatically when the housing and the first swing arm reach a predetermined relative position, a second lock device for locking a relative rotational motion of the first and second swing arms automatically when the first and second swing arms vertically reach a position where the two overlap each other, and a lock setting device for switching the first and second lock devices in one behavior to a lockable state able to effect locking automatically in the predetermined relative position and the overlapping position or an unlockable state failing to perform the locking in the predetermined relative position and the overlapping position.

In the invention according to the first aspect, locking is made automatically at the predetermined position in the lockable state, while in the unlockable state the motion of the first swing arm and that of the second swing arm are rendered natural and switching from one to the other of these states is done simply in one behavior.

In a second aspect of the invention there is provided, in combination with the above first aspect, a display support arm wherein the second and third swing arms are provided vertically above the first swing arm.

In the invention according to the second aspect, the second and third swing arms can be stacked easily.

In a third aspect of the invention there is provided, in combination with the above first or second aspect, a display support arm wherein the first lock device includes a plunger hole formed in a joining surface of the first end portion for joining to the housing, the plunger hole extending vertically, a plunger disposed within the plunger hole and having a first rod movable vertically, and a first rod hole for insertion therein of the first rod, the first rod hole being formed in a joining surface of the housing confronting the joining surface of the first end portion.

In the invention according to the third aspect, the first lock device can lock the rotational motion between the housing and the first swing arm.

In a fourth aspect of the invention there is provided, in combination with any of the above first to third aspects, a display support arm wherein the second lock device includes a rod-like hook projecting vertically upwards from the first swing arm and a fitting portion for fitting with an upper end portion of the hook, the fitting portion being formed on the surface of the second swing arm confront the first swing arm.

In the invention according to the fourth aspect, the second lock device can lock the relative rotational motion between the first and second swing arms.

In a fifth aspect of the invention there is provided, in combination with the above fourth aspect, a display support arm wherein the lock setting device includes a hook rotating device for switching by rotation the rod-like hook mounted to the first swing arm to the projecting state as the lockable state or a state as the unlockable state in which the rod-like hook extends along an arm of the first swing arm.

In the invention according to the fifth aspect, the hook is rotated and switching is made between the lockable state and the unlockable state.

In a sixth aspect of the invention there is provided, in combination with the above fifth aspect, a display support arm wherein the hook rotating device includes a rotary knob for performing the rotation manually, the rotary knob being mounted to a side face of the first swing arm.

In the invention according to the sixth aspect, switching is made manually by the rotary knob between the lockable state and the unlockable state.

In a seventh aspect of the invention there is provided, in combination with the above fifth or sixth aspect, a display support arm wherein the hook rotating device includes a resilient member for maintaining the projecting state and the extending-along-the-arm state with resilience.

In the invention according to the seventh aspect of the invention, the hook rotating device makes the rod-like hook assuming the projecting state somewhat rotatable with use of an external force.

In an eighth aspect of the invention there is provided, in combination with any of the above fifth to seventh aspects, a display support arm wherein the hook rotating device includes a link device for bringing the plunger into a vertically raised state as the unlockable state and a vertically lowered state as the lockable state in synchronism with the switching operation.

In the invention according to the eighth aspect, the plunger is switched between the lockable state and the unlockable state by the link device.

In a ninth aspect of the invention there is provided, in combination with any of the above fourth to eighth aspects, a display support arm wherein the fitting portion includes an opening in a direction along an arm of the second swing arm, the opening serving as an inlet of the fitting, and a guide surface formed around the opening, the guide surface having an oblique inclination with respect to the direction.

In the invention according to the ninth aspect, the fitting portion has a shape which permits the upper end portion of the rod-like hook to be fitted therein under any rotation.

In a tenth aspect of the invention there is provided, in combination with the above ninth aspect, a display support arm wherein the guide surface is disposed on a circular path, the circular path being described by the projecting position of the rod-like hook present on the first swing arm when the first swing arm is rotated with the second end portion as a rotational center.

In the invention according to the tenth aspect, the upper end portion of the rod-like hook is brought into contact with the guide surface with rotation of the first and second swing arms.

In an eleventh aspect of the invention there is provided, in combination with any of the above fourth to tenth aspects, a display support arm wherein the display includes a third swing arm having a fifth end portion joined to the fourth end portion vertically downward and further having a sixth end portion, the third swing arm causing the display positioned at the sixth end portion to rotate in a horizontal plane.

In the invention according to the eleventh aspect, the direction of the display with respect to the second swing arm is changed.

In a twelfth aspect of the invention there is provided, in combination with the above eleventh aspect, a display support arm further comprising a third lock device for locking the rotational motion of the second swing arm and that of the third swing arm automatically when the lock setting device is in its lockable stage and when the second and third swing arms perform a relative rotational motion and reach a predetermined relative position in case of the upper end portion of the hook and the fitting portion being fitted together.

In the invention according to the twelfth aspect, a relative rotational motion between the second and third swing arms is made lockable simultaneously with locking between the first and second swing arms.

In a thirteenth aspect of the invention there is provided, in combination with the above twelfth aspect, a display support arm wherein the third lock device includes a second rod and a second rod hole formed in a side face of the fifth end portion for insertion therein of the rod, the second rod being disposed in the opening of the fitting portion and movable in the direction of the arm of the second swing arm while penetrating the fitting portion when the fitting portion is positioned near the side face of the fifth end portion.

In the invention according to the thirteenth aspect, the third lock device makes locking with movement of the second rod disposed in the fitting portion.

In a fourteenth aspect of the invention there is provided, in combination with any of the above first to thirteenth aspects, a display support arms wherein the display includes a rotating device for rotating the display around a horizontal rotary shaft orthogonal to a direction along an arm of the third swing arm.

In the invention according to the fourteenth aspect, the display surface of the display is set at an angle easy to see for an operator and is positioned so as to confront the housing, whereby it is protected against an external shock.

In a fifteenth aspect of the invention there is provided an ultrasonic imaging apparatus comprising a first swing arm having a first end portion positioned vertically on top of a housing and further having a second end portion, the first swing arm causing the second end portion to rotate in a horizontal plane with the first end portion as a rotational center, a second swing arm having a third end portion joined vertically to the second end portion and further having a fourth end portion, the second swing arm causing the fourth end portion to rotate in a horizontal plane with the third end portion as a rotational center, a display joined vertically to the fourth end portion, a first lock device for locking a rotational motion of the first swing arm automatically when the housing and the first swing arm reach a predetermined relative position, a second lock device for locking a relative rotational motion of the first and second swing arms automatically when the first and second swing arms vertically reach a position where the two overlap each other, and a lock setting device for switching the first and second lock devices in one behavior to a lockable state able to effect locking automatically in the predetermined relative position and the overlapping position or an unlockable state failing to perform the locking in the predetermined relative position and the overlapping position.

In a sixteenth aspect of the invention there is provided, in combination with the above fifteenth aspect, an ultrasonic imaging apparatus wherein the display includes a third swing arm having a fifth end portion joined to the fourth end portion vertically downward and further having a sixth end portion, the third swing arm causing the display positioned at the sixth end portion to rotate in a horizontal plate.

In a seventeenth aspect of the invention there is provided, in combination with the above sixteenth aspect, an ultrasonic imaging apparatus further comprising a third lock device for locking the rotational motion of the second swing arm and that of the third swing arm automatically when the lock setting device is in its lockable state and when the second and third swing arms perform a relative rotational motion and reach a predetermined relative position in case of the second lock device being locked.

According to the invention, the lock setting device can make switching in one behavior between the lockable state and the unlockable state, and when the lockable state is established by the lock setting device, the rotational motion is locked automatically during the relative rotational motion of the first, second and third swing arms positioned on the housing and upon arrival of the arm position at the predetermined relative position, while when the unlockable state is established by the lock setting device, a free rotation of the arms is ensured during imaging using the ultrasonic imaging apparatus and independently of the presence of the lock mechanism. Therefore, the arms can each be locked easily at a predetermined position by its rotational motion without deteriorating the operating performance of the operator during imaging. Consequently, a preparatory procedure at the time of movement of the ultrasonic imaging apparatus is simplified and it is possible to eliminate a trouble caused by shaking or the like of the display during movement.

Further objects and advantages of the present invention will be apparent from the following description of the preferred embodiments of the invention as illustrated in the accompanying drawings.

BRIEF DESCRIPTION OF THE DRAWINGS

FIGS. 11(a) and 11(b) are explanatory diagrams showing the operation of the third lock device.

DETAILED DESCRIPTION OF THE INVENTION

A display support arm and an ultrasonic imaging apparatus of this invention will be described by way of example with reference to the accompanying drawings. However, it is not intended as a definition of the limits of the invention.

Figure 1:
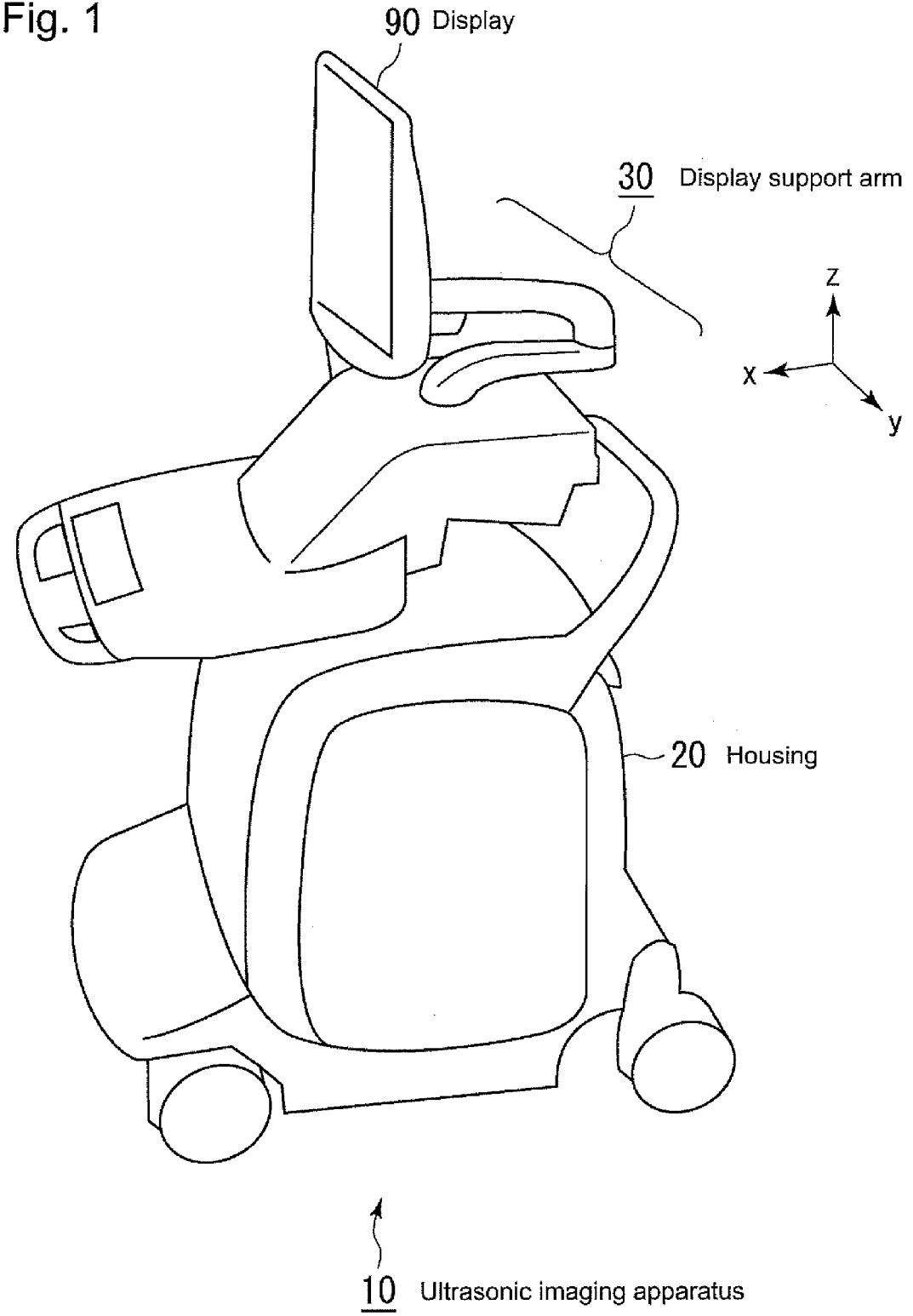
FIG. 1 is an appearance diagram showing the configuration of an ultrasonic imaging apparatus.

First, the configuration of an ultrasonic imaging apparatus 10 according to an embodiment of the invention will be described with reference to FIG. 1. FIG. 1 is a configuration diagram showing the configuration of the ultrasonic imaging apparatus 10. The ultrasonic imaging apparatus 10 includes a display support arm 30 and a display 90. The housing 20 includes a transmitter/receiver section for transmission and reception of electric signals, an image processing section for generating image information with use of a received electric signal, a cine memory section for storage of the image information, and an image display control section for controlling the display of image on the display 90. An ultrasonic probe (not shown) is connected to the housing 20 through a coaxial cable. The ultrasonic probe includes a piezoelectric element, generates an ultrasonic wave proportional to the electric signal from a surface of contact with a subject and acquires intra-body information of the subject. The xyz-axis coordinates shown in FIG. 1 and subsequent figures represent the same directions in all the drawings and clearly show relative positional relations among the drawings.

The housing 20 has wheels mounted to a lower portion thereof and can be easily moved by an operator's manual operation using a handle attached to the housing backward from side faces of the housing. Thus, the movement of the ultrasonic imaging apparatus 10 in a hospital, for example, the movement thereof between bedsides, can be done quickly.

The display 90 is constituted by a light-weight display such as LCD. Intra-body information of the subject is mainly displayed on the display 90.

The display support arm 30 is placed vertically on top of the housing 20 and is supported movably by plural swing arms. With the display support arm 30, the operator can observe the display 90 at a position somewhat spaced away from the housing 20.

Figure 2:
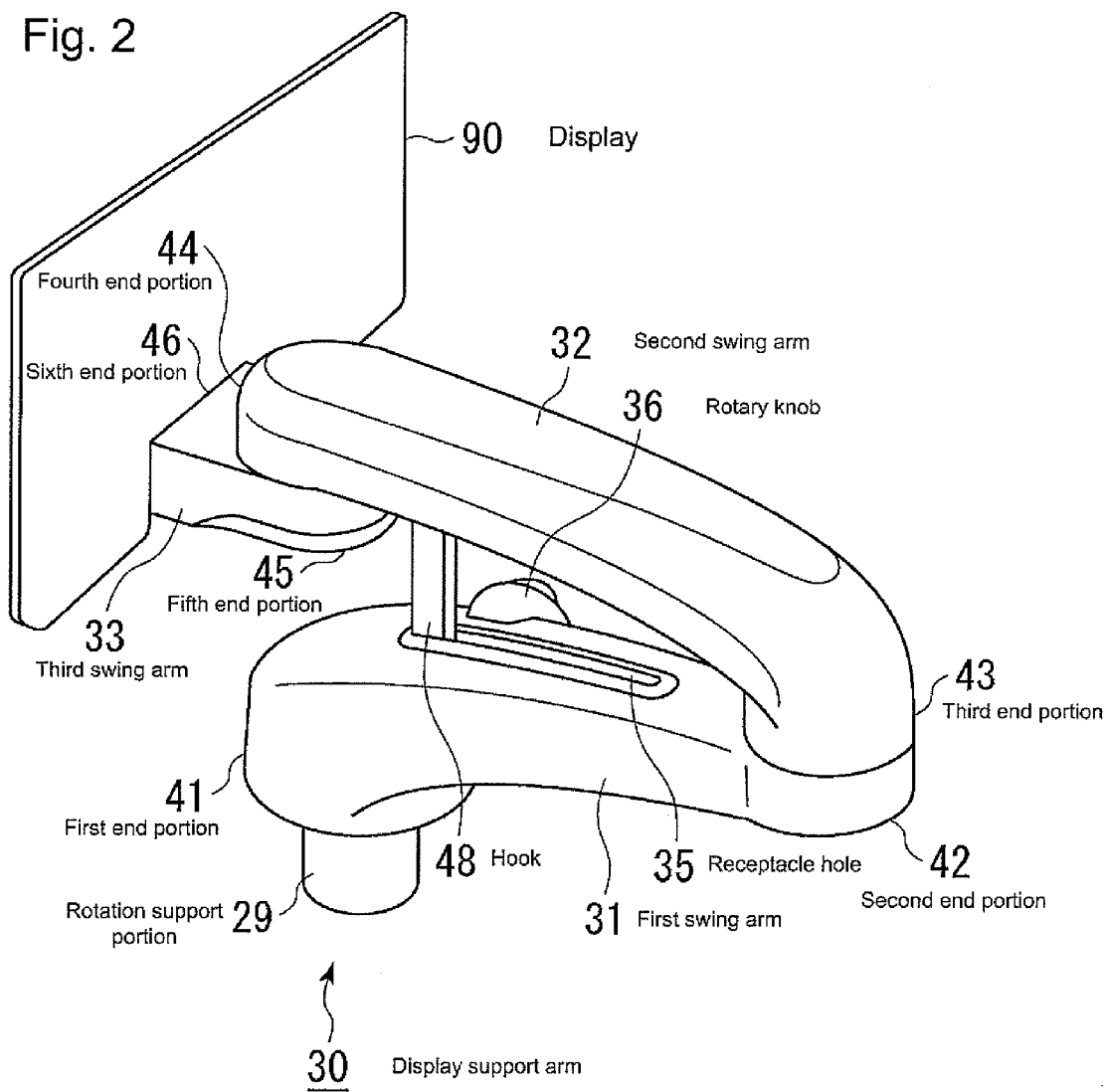
FIG. 2 is an appearance diagram showing an appearance of a display support arm (part 1).

FIG. 2 is an appearance diagram showing an appearance of the display support arm 30 in a locked state as seen obliquely from above. The display support arm 30 includes a first swing arm 31, a second swing arm 32, a third swing arm 33, a first lock device, a second lock device, a third lock device, and a lock setting device (not shown). As to the first to third lock devices and the lock setting device (not shown), a detailed description will be given later.

The first swing arm 31 includes a rotation support portion 29, a first end portion 41, a second end portion 42, a receptacle hole 35, a rod-like hook 48 and a rotary knob 36. The hook 48 constitutes a part of the first lock device to be described later, while the receptacle hole 35 and the rotary knob 36 constitute a part of the lock setting device (not shown).

The rotation support portion 29 is buried into a mounting surface of the first end portion positioned vertically on top of the housing 20. The first swing arm 31 is held rotatably in the horizontal plane with the rotation support portion 29 as a rotational center. The other end portion, i.e., the second end portion 42, of the first swing arm 31 moves on a circular path in the horizontal plane centered on the first end portion 41.

The hook 48 has a locking function of preventing a rotational movement between the first and second swing arms 31, 32 at such a relative position as shown in FIG. 2 where the first and second arms 31,32 overlap each other. The rotary knob 36 as a hook rotating device causes the rod-like hook 48 to rotate in a direction along an arm of the first swing arm 31, i.e., in the xz-axis plane shown in FIG. 2, and causes it to be received within the receptacle hole 35 extending along the first swing arm 31.

The second swing arm 32 has a third end portion 43 and a fourth end portion 44 at both ends of its arm. The third end portion 43 is held vertically above the second end portion 42 of the first swing arm 31 so as to be relatively rotatable in the horizontal plane. The other end portion, i.e., the fourth end portion 44, of the second swing arm 31 moves on a circular path in the horizontal plane centered on the third end portion 43.

The third swing arm 33 has a fifth end portion 45 and a sixth end portion 46 at both ends of its arm. The fifth end portion 45 is held vertically below the fourth end portion 44 of the second swing arm 32 so as to be relatively rotatably in the horizontal plane. The other end portion, i.e., the sixth end portion 46, of the third swing arm 33 moves on a circular path in the horizontal plane centered on the fifth end portion 45.

The display 90 such as LCD is mounted to the sixth end portion 46 of the third swing arm 33. For positioning the display surface of the display 90 in a direction easy to see for the operator and for protecting the display surface, the third swing arm 33 has a display rotating device (not shown) which has a rotary shaft in a horizontal direction orthogonal to the arm of the third swing arm 33.

Figure 3:
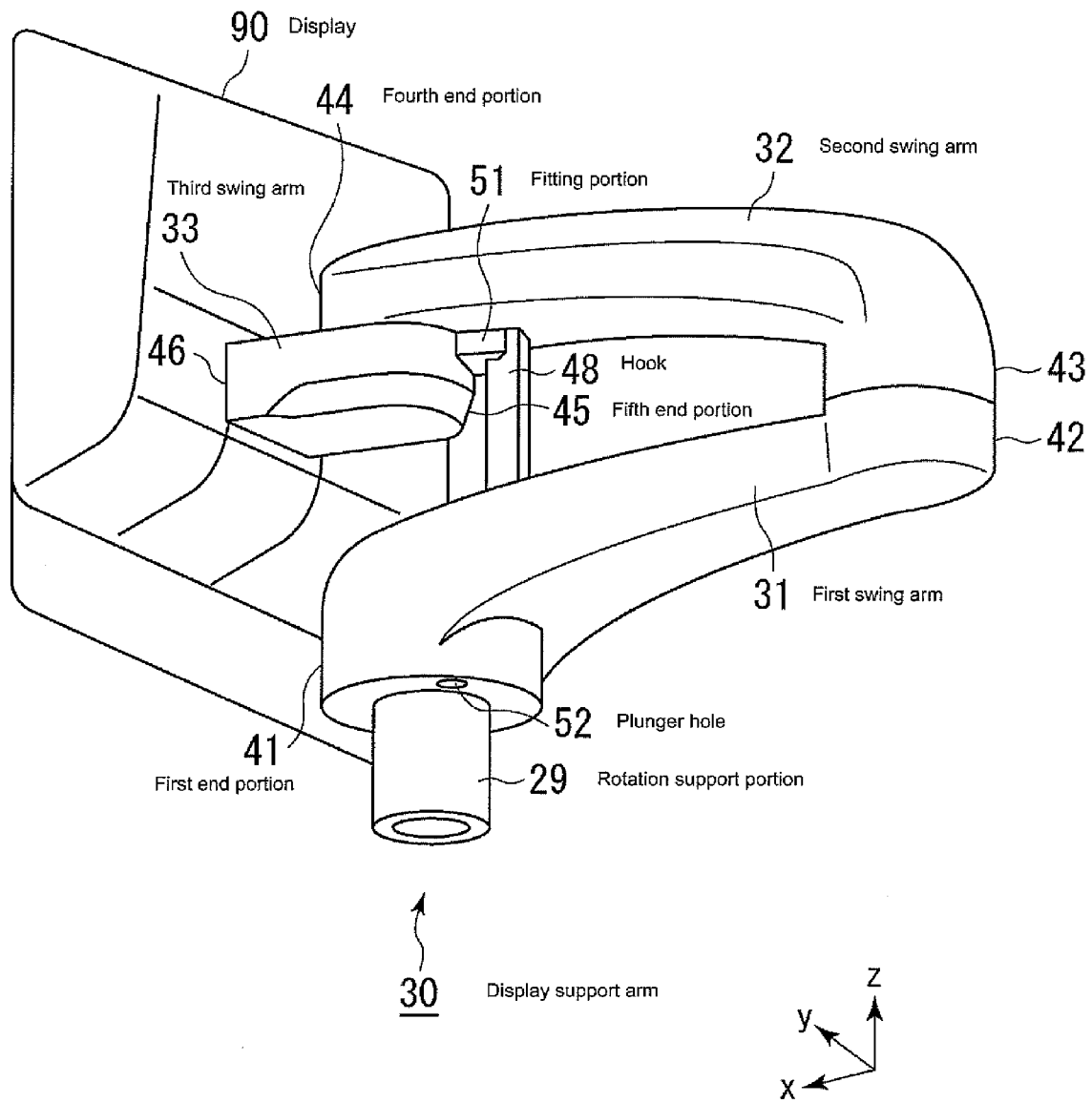
FIG. 3 is an appearance diagram showing an appearance of the display support arm (part 2).

FIG. 3 is an appearance diagram showing an appearance of the display support arm 30 in a locked state as seen obliquely from below. In FIG. 3 there is shown a structure which is substantially the same as the appearance of FIG. 2 as seen obliquely from above. A point different from FIG. 2 is that a plunger hole 52 formed in the first end portion 41 and a fitting portion 51 of the second swing arm 32 are shown.

The plunger hole 52 is formed in the surface of the first end portion 41 which surface is put in contact with the housing 20. A plunger (not shown) is disposed within the plunger hole 52 so as to be vertically movable as will be described later. In the contact surface of the housing 20 opposed to the plunger hole 52 is formed a first rod hole (not shown) at a predetermined position for insertion therein of a first rod (not shown) of the plunger 62.

The fitting portion 51 is fixed to the surface of the second swing arm 32 opposed to the first swing arm 31 and is fitted with an upper end portion of the rod-like hook 48. This fitting prevents a relative rotational motion in the horizontal plane between the first and second swing arms 31, 32. The fitting portion 51 is positioned close to a side face of the fifth end portion 45 and incorporates a third lock device for locking a relative rotational motion between the second and third swing arms 32, 33 as will be described later.

Figure 4:
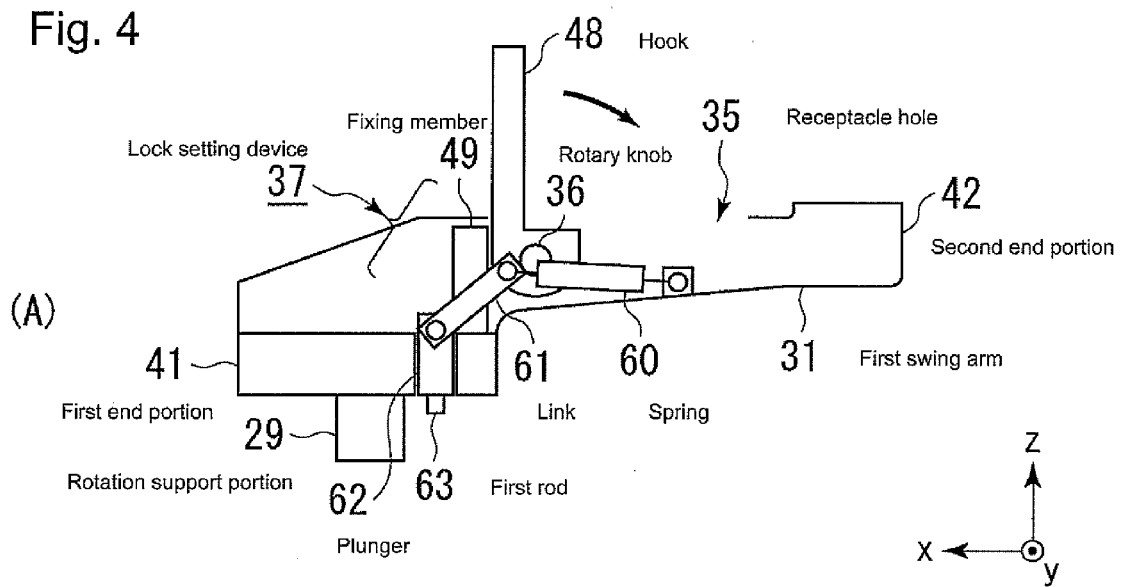
FIGS. 4(a) and 4(b) are sectional views showing a section of a first swing arm including a first lock device, a second lock device and a lock setting device.
Figure 4:
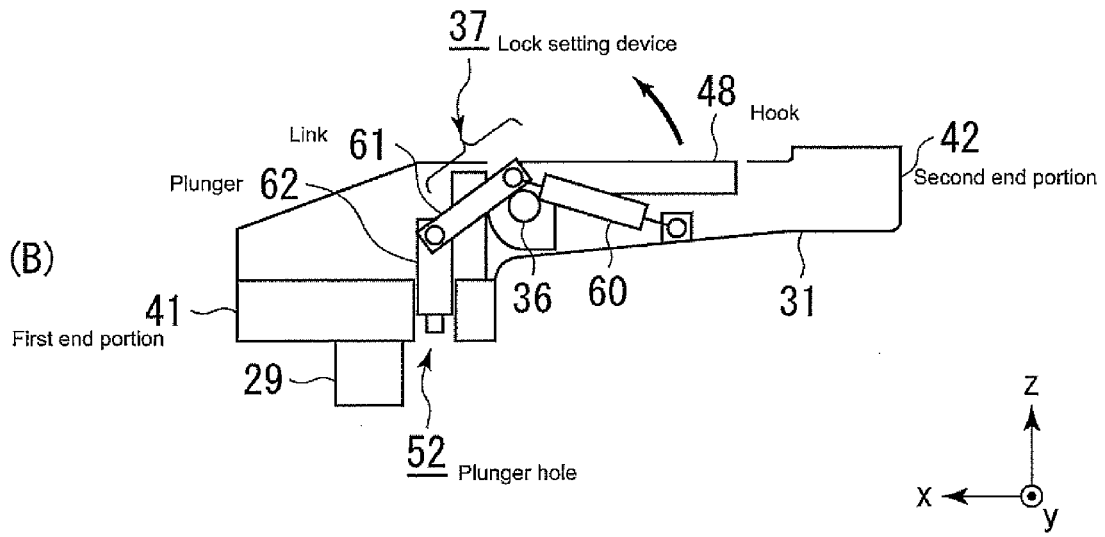

FIG. 4 is a sectional view of the first swing arm 31, showing the first lock device, the second lock device and the lock setting device 37 which are mounted to the first swing arm 31. The section of FIG. 4 is the xz-axis section taken along the arm of the first swing arm 31.

The first lock device includes the plunger 62 and a first rod hole formed in the surface of contact of the housing 20 with the first end portion 41 for insertion therein of the first rod 63 of the plunger 62. The second lock device includes the hook 48, a fixing member 49 and the fitting portion (not shown) present on the second swing arm 32.

The lock setting device 37 includes the rotary knob 36 as a hook rotating device, a spring 60 as a resilient member and a link 61 as a link device. The rotary knob 36 as a hook rotating device shown also in FIG. 2 is mounted to a side face of the first swing arm 31 and is integral with the hook 48, causing the hook 48 to rotate in the xz-axis plane. With this rotation, the hook 48 is switched between the state as a lockable state in which it is projected to the second swing arm 32 side perpendicularly to the arm direction of the first swing arm 31 and the state as an unlockable state in which it faces the arm direction of the first swing arm 31 and is substantially received within a receptacle hole 35 of the first swing arm 31. This switching operation is completed in one behavior by rotation of the rotary knob 36 performed by the operator. The fixing member 49 functions to keep the rod-like hook 48 projected from the first swing arm 31.

FIG. 4(A) illustrates the state in which the rod-like hook 48 is projected to the second swing arm 32 side perpendicularly to the arm direction of the first swing arm 31. FIG. 4(B) illustrates the state in which the rod-like hook 48 faces the arm direction of the first swing arm 31 and is substantially received within the first swing arm 31.

The spring 60 as a resilient member is disposed near the position where the rod-like hook 48 and the rotary knob 36 are connected with each other. One end of the spring 60 is fixed near the connected position of both rod-like hook 48 and rotary knob 36 and the other end thereof is fixed to the wall surface of the first swing arm 31. Consequently, in such a state as shown in FIG. 4(A) in which the rod-like hook 48 is projected in the vertical direction, the rod-like hook 48 is pushed against the fixing member 49 with resilience. Therefore, for example when an external force is applied to the upper end portion of the rod-like hook 48 from the side where the fixing member 49 is present, the rod-like hook 48 is deviated from the vertical direction, rotates clockwise easily about the rotary knob 36 and moves to a position where the external force balances with the force of the spring 60 acting to push the rod-like hook 48 against the fixing member 49. On the other hand, upon removal of the external force applied to the upper end portion of the rod-like hook 48, the hook 48 rotates counterclockwise by virtue of the spring 60 and returns to the position where it faces the vertical direction.

The plunger 62 which lies in the plunger hole 52 is connected to the hook 48 through the link 61. The plunger 62 incorporates the first rod 63 which projects toward the housing 20 by virtue of a spring member installed in the interior of the plunger. The first rod 63 is press-fitted into the interior of the plunger 62 with pressure exerted thereon from the housing 20 side. On the other hand, upon removal of the pressure exerted from the housing 20 side, the first rod 63 again assumes its projected state.

With the link 61 as a link device, the plunger 62 moves vertically through the plunger hole 52 in synchronism with rotation of the hook 48. As shown in FIG. 4(A), when the rod-like hook 48 is in its vertically projected state, the plunger 62 is in its vertically lowered state and the first rod 63 assumes a projectable state toward the housing 20 from the surface of contact of the first end portion 41 with the housing 20. On the other hand, as shown in FIG. 4(B), when the rod-like hook 48 faces the horizontal direction and is received within the first swing arm 31, the plunger 62 assumes a vertically raised position and the first rod 63 itself is depressed into the plunger hole 52 from the surface of contact of the first end portion 41 with the housing 20.

Figure 5:
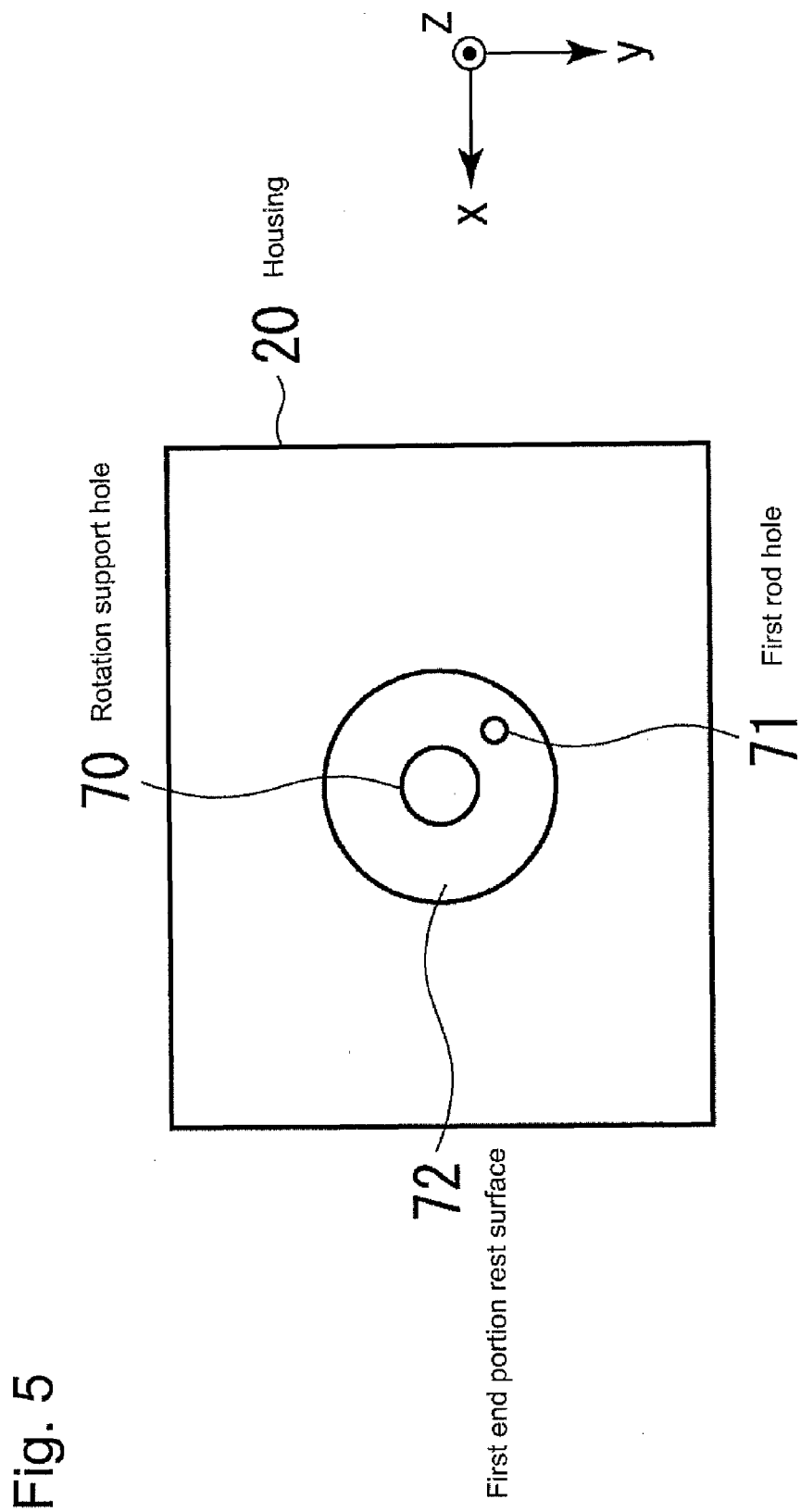
FIG. 5 is a plan view showing a rest surface of a housing for resting a first end portion thereon.

FIG. 5 is a plan view of a joining surface of the housing 20 as seen vertically from above, the joining surface lying at a vertical top position of the housing with the first swing arm 31 placed thereon. A first end portion rest surface 72 is provided in the portion of the housing where the first end portion 41 of the first swing arm 31 is rested. A rotation support hole 70 for insertion therein of the rotation support portion 29 is formed centrally of the first end portion rest surface 72. Further, the first rod hole 71 for insertion therein of the first rod 63 of the plunger 62 is formed in the first end portion rest surface 72. The first rod hole 71 is formed in a position where it overlaps the plunger hole 52 of the first end portion 41 for example when the arm direction of the first swing arm 31 lies in a home position where it faces the front side of the ultrasonic imaging apparatus. In this case, the first rod 63 of the plunger 62 lying in the plunger hole 52 is inserted automatically into the overlapped first rod hole 71, whereby the housing 20 and the first swing arm 31 are locked.

Figure 6:
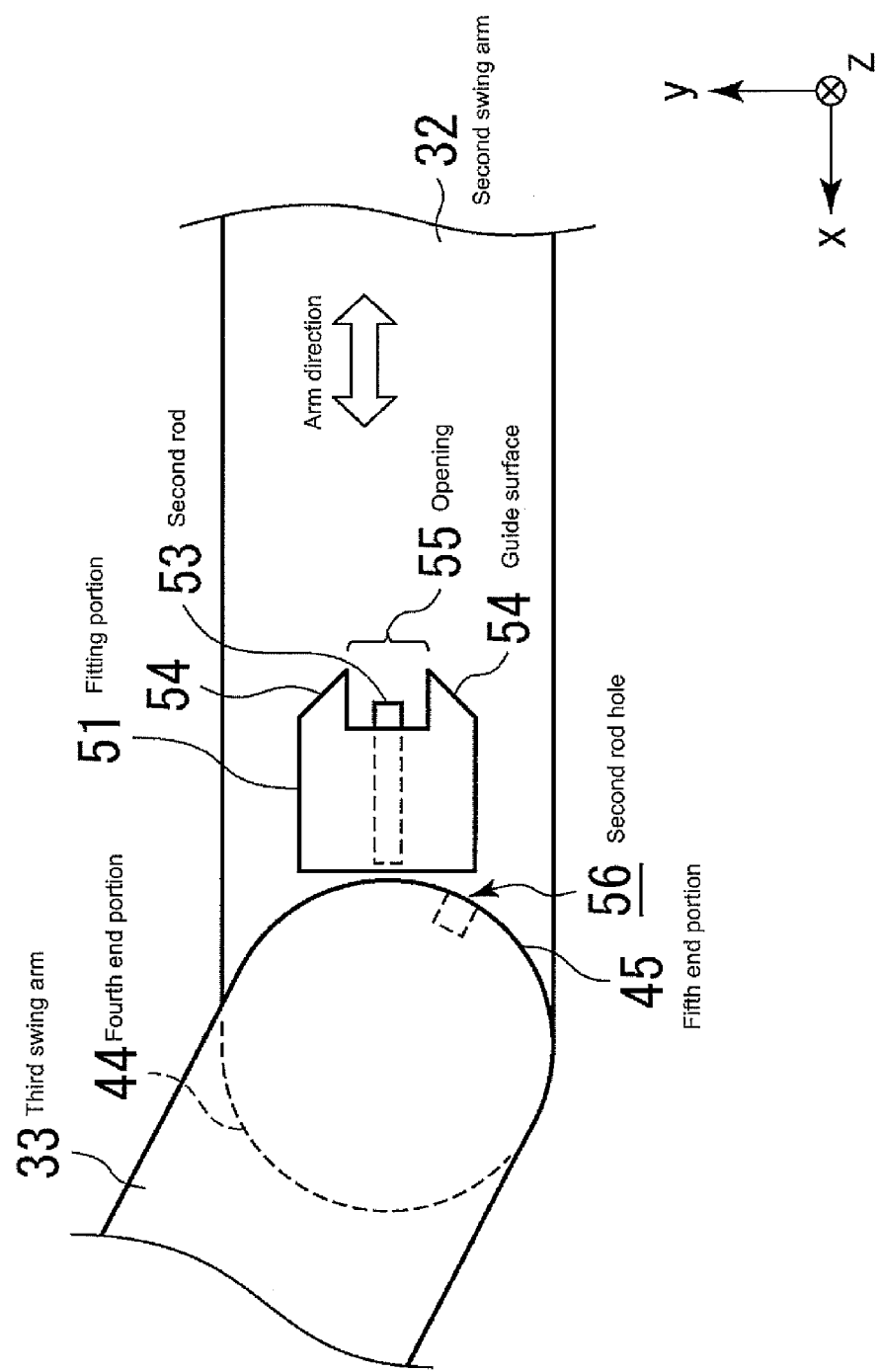
FIG. 6 is an explanatory diagram showing a third lock device including a fitting portion and a second rod hole.

FIG. 6 is an explanatory diagram showing the third lock device for locking a relative rotational motion in the horizontal plane of both second and third swing arms 32, 33. The third lock device includes the fitting portion 51, a second rod 53 and a second rod hole 56.

The fitting portion 51 is disposed in proximity to the third swing arm 33 and includes the second rod 53, a guide surface 54 and an opening 55. The opening 55 serves as an inlet port when holding therein the upper end portion of the rod-like hook 48 as in FIG. 3. The opening 55 faces a direction along the arm of the second swing arm 32 and opens in a direction opposite to the fourth end portion 44 where the third swing arm 33 is present.

The guide surface 54 is present around the opening 55. The guide surface 54 has an angle inclined obliquely relative to the direction along the arm of the second swing arm 32. The guide surface 54 lies on a rotational path which the upper end portion of the rod-like hook 48 projecting in the direction of the second swing arm 32 describes when the first and second swing arms 31, 32 perform a relative rotational motion. Therefore, the upper end portion of the rod-like hook 48 comes into contact with the guide surface 54 of the fitting portion 51 in the vicinity of the position where the first and second swing arms 31, 32 overlap each other when both arms perform a relative rotational motion.

The second rod 53 lies in the interior of the opening 55. The fitting portion 51 is provided in the interior thereof with a spring member and has a plunger structure for pushing out the second rod 53 toward the opening 55. The second rod 53 is movable in the direction along the arm of the second swing arm 32 and projects to the opening 55 side when there is no external force acting along the arm.

The second rod 59 is set at a length such that in its projected state to the opening 55 side there occurs no projection on the side of the fitting portion 51 where the third swing arm 33 is present. When the projecting portion of the second rod 53 on the opening 55 side is pushed by an external force and moves toward the third swing arm 33, the second rod 53 projects to the third swing arm 33 side.

The second rod hole 56 is formed in the side face of the third swing arm 33 located close to the fitting portion 51. The second rod hole has a diameter equal to the diameter of the second rod 53 and lies in the same vertical position as the second rod 53 in the fitting portion 51. The position in the horizontal plane of the second rod hole 56 is set at the position where the second rod hole 56 is aligned with the second rod 53 when the arms of the second and third swing arms 32, 33 face the same direction.

Figure 7:
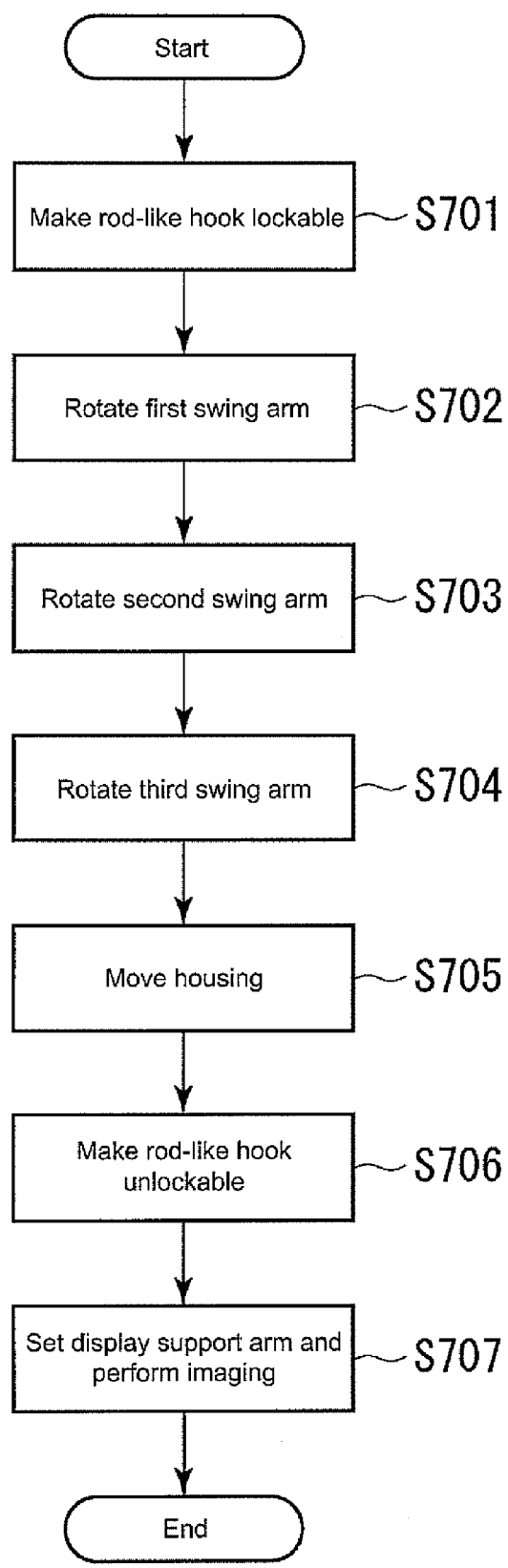
FIG. 7 is a flow chart showing the operation of a display support arm embodying the invention.
Figure 8:
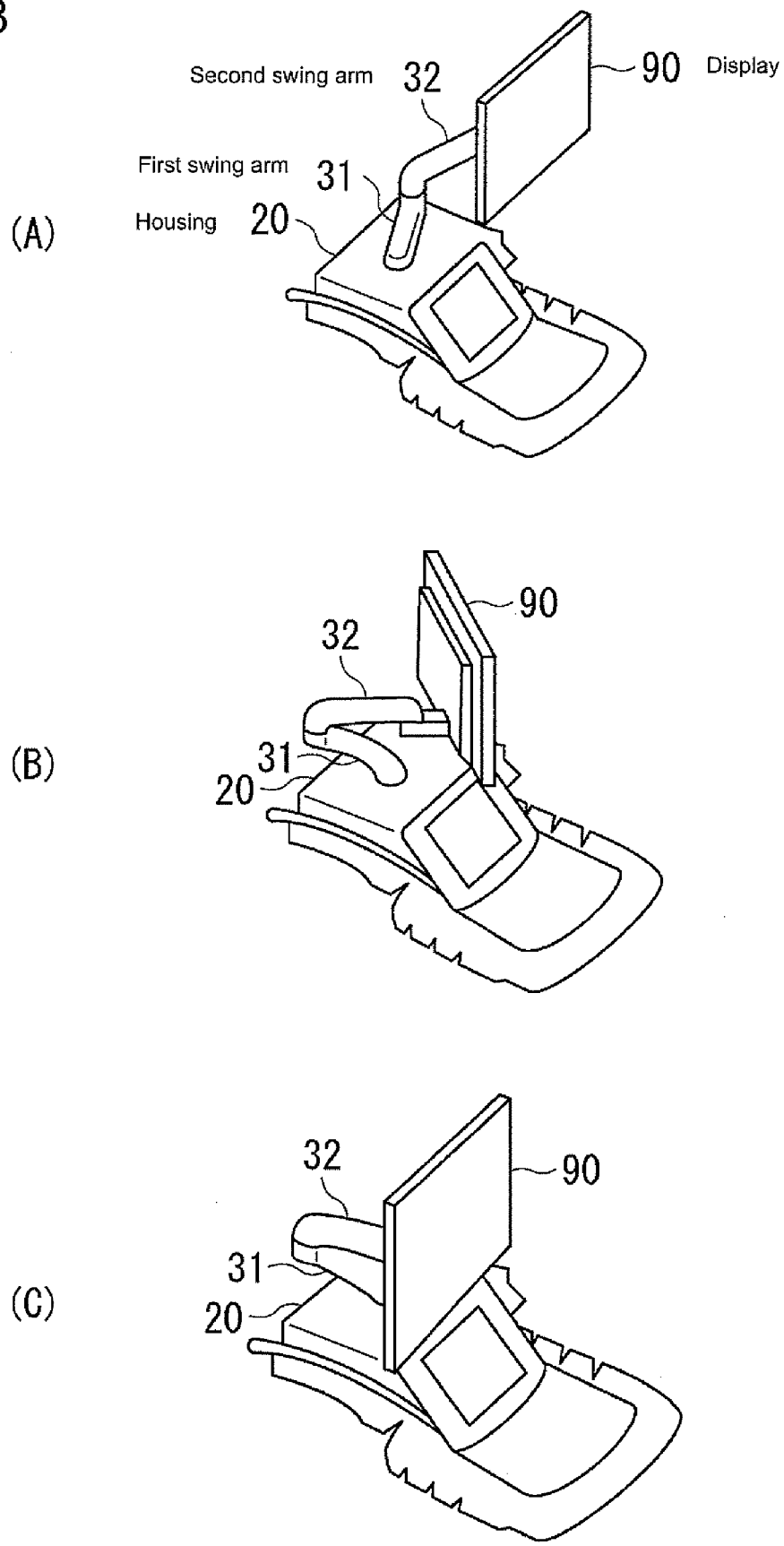
FIGS. 8(a), 8(b), and 8(c) are appearance diagrams showing operational conditions of the display support arm.

Next, the operations of the first to third lock devices and the lock setting device 37 as constituents of the display support arm 30 will be described with reference to FIGS. 7 to 11. FIG. 7 is a flow chart explaining the operation of the display support arm 30 and FIG. 8 illustrates the state of the display support arm 30 in main operation steps shown in the flow chart of FIG. 7.

First, the display support arm 30 picks up an image of the subject with use of the ultrasonic imaging apparatus 10 and is brought into a state in which the first, second and third swing arms 31, 32, 33 face different directions. FIG. 8(A) illustrates the display support arm 30 which assumes this state. The first to third swing arms 31 to 33 face different directions and the display 90 is disposed at a position away from the housing 20.

Turning back to FIG. 7, the operator causes rotation of the rotary knob 36 as the lock setting device 37 mounted to a side face of the first swing arm 31 and brings the rod-like hook 48 into the lockable state in which the hook projects vertically from the first swing arm 31 (step S701). As shown in FIG. 4(A), the plunger 52 descends through the plunger hole 52 as soon as the rod-like hook 48 assumes its vertically projecting state from the first swing arm 31, and the first rod 63 of the plunger 62 tends to project downward from the surface joined to the housing 20. However, since the first swing arm 31 is rested on the housing 20, the first rod 63 comes into contact with the first end portion rest surface 72 of the housing 20 and is pushed back into the interior of the plunger 62.

Figure 9:
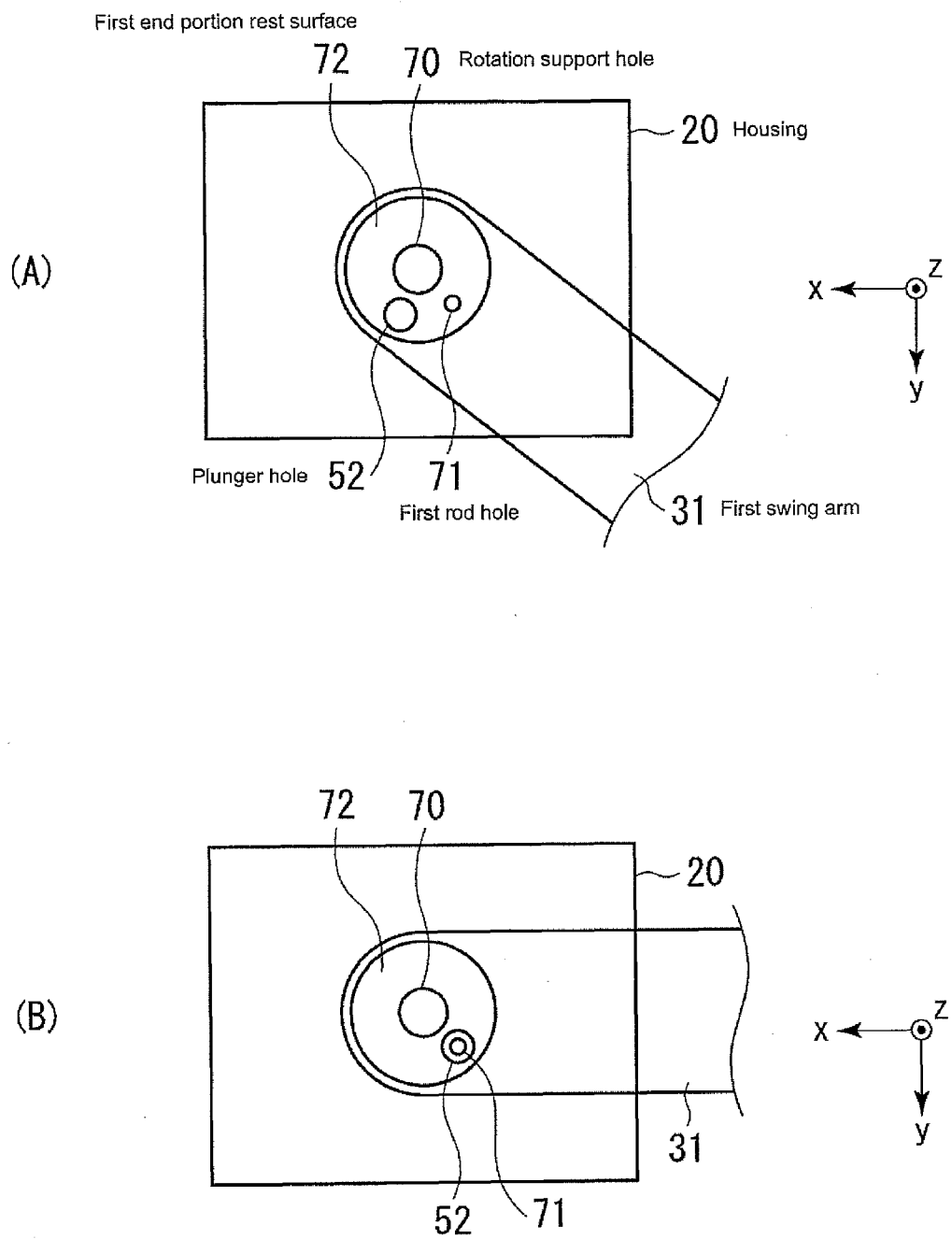
FIGS. 9(a) and 9(b) are explanatory diagrams showing the operation of the first lock device.

Thereafter, the operator causes the first swing arm 31 to rotate toward the home position, for example, in the direction in which the arm faces the front side of the ultrasonic imaging apparatus 10 (step S702). FIG. 9 is an explanatory diagram for explaining this operation in which the housing 20 and the first swing arm rested on the housing are seen vertically from above. In the same figure, the first rod hole 71 and the plunger hole 52 are described see-throughwise in order to facilitate understanding.

FIG. 9(A) illustrates a case where the arm of the first swing arm 31 is inclined relative to the front side direction of the housing 20. The first rod hole 71 lies in the first end portion rest surface 72, while the plunger hole 52 lies in the first swing arm 31. In FIG. 9(A), the first rod hole 71 and the plunger hole 52 lie in different positions. Therefore, the first rod 63 of the plunger 62 which lies in the interior of the plunger hole 52 is in a pushed-back state into the interior of the plunger 62 and is not in its locked state that obstructs its rotational motion.

FIG. 9(B) illustrates a case where the arm of the first swing arm is brought into a state in which it faces the front side direction of the housing 20 with a rotational motion performed by the operator. In this case, the plunger hole 52 and the first rod hole 71 assume an overlapped state. Thus, the first rod 63 and the first rod hole 71 lie in their overlapped position and the first rod 63 enters automatically into the first rod hole 71 by virtue of the resilient material of the plunger 62. As a result, the relative rotational motion of the housing 20 and the first swing arm 31 assumed a locked state and stops. In FIG. 8(B) there is shown the display support arm 30 with both housing 20 and first swing arm 31 locked.

Figure 10:
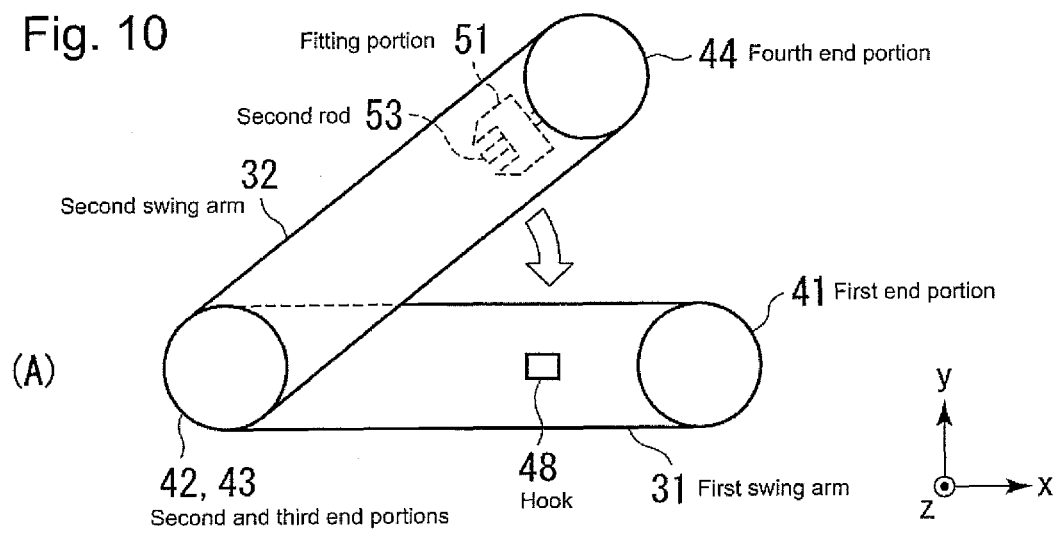
FIGS. 10(a), 10(b), and 10(c) are explanatory diagrams showing the operation of the second lock device.
Figure 10:
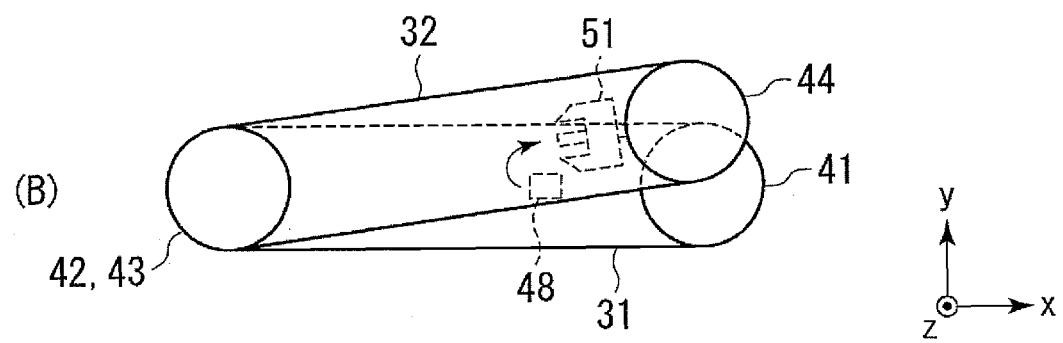
Figure 10:
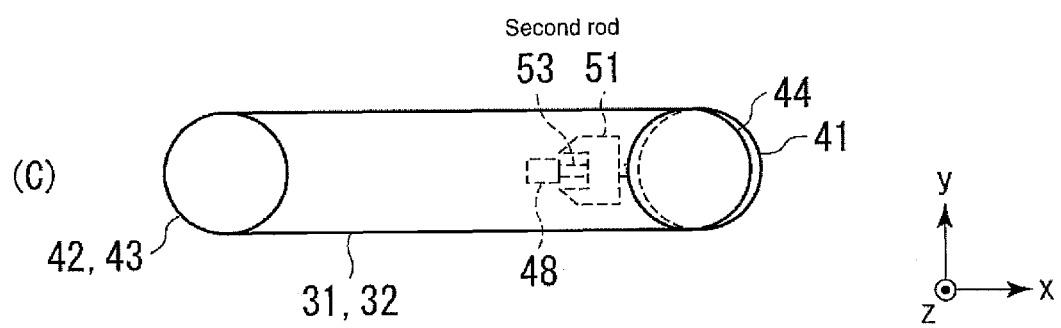

Turning back to FIG. 7, the operator then causes the second swing arm 32 to rotate toward the home position, for example in a direction in which the arm faces the same direction of the first swing arm 31 (step S703). FIG. 10 is an explanatory diagram in which a relative rotational motion of the first and second swing arms 31, 32 is seen vertically from above. In the same figure, only the upper end portion of the rod-like hook 48 and the fitting portion 51 are partially described in order to facilitate understanding.

FIG. 10(A) shows a case where the arm of the second swing arm is at an angle inclined in the horizontal plane relative to the arm of the first swing arm 31. The first and second swing arms 31, 32 perform a rotational motion centered at the second and third end portions 42, 43 overlapped each other.

FIG. 10(B) illustrates a state in which the first and second swing arms 31, 32 are close to each other and the fitting portion 51 and the upper end portion of the rod-like hook 48 are in contact with each other. The hook 48 comes into contact with the guide surface 54 positioned around the opening 55 of the fitting portion 51.

The guide surface 54 has an angle inclined obliquely in the horizontal plane relative to the arm direction of the second swing arm 32. As shown in FIG. 4(A), the rod-like hook 48 is fixed under the resilience of the spring 60, and in the direction of the second end portion 42 along the first swing arm 31 the rod-like hook 48 tilts easily while retaining its restoring force. With a further continued rotational motion, the rod-like hook 48 in contact with the guide surface 54 gets over the guide surface 54 while sliding laterally on the guide surface in the direction of the second end portion 42 and is fitted in the opening 55.

FIG. 10(C) shows a state in which the rod-like hook 48 is fitted in the fitting portion 51. In this state, the first and second arms 31, 32 assumed their locked state and a relative rotational motion thereof is inhibited. With the restoring force of the rod-like hook 48, the second rod 53 in the fitting portion 51 is pushed toward the first end portion 41. However, side faces of the fitting portion 51 and the fifth end portion 45 are close to each other and the movement of the second rod 53 and the movement of the second rod 53 is only a small movement and stops in a state in which the end face of the second rod 53 on the first end portion 41 side holds down the side face of the fifth end portion 45.

Turning back to FIG. 7, the operator then causes the third swing arm 33 to rotate toward the home position, for example in a direction in which the arm faces the same direction as the first and second swing arms 31, 32 (step S704). FIG. 11 is an explanatory diagram in which a relative rotational motion of the second and third swing arms 32, 33 is seen vertically from above. In the same figure, only the fitting portion 51 and the second rod hole 56 are partially described in order to facilitate understanding.

FIG. 11(A) shows a case where the arm of the second swing arm 32 faces a different direction inclined in the horizontal plane relative to the arm of the third swing arm 33. The second and third swing arms 32, 33 perform a rotational motion centered at the fourth and fifth end portions overlapped each other. The second rod 53 is pushed against the fourth end portion 44 by the rod-like hook 48, but abuts itself against a side face of the fifth end portion 45 and moves only slightly.

FIG. 11(B) shows a state in which with a rotational motion the third swing arm 33 comes to face the same direction as the second swing arm 32, and the second rod hole 56 and the second rod 53 are aligned with each other in the horizontal plane. The second rod 53 is pushed by the rod-like hook 48 and enters the interior of the second rod hole 56. Further, the relative rotational motion of the second and third swing arms 32, 33 is locked and stopped. FIG. 8(C) shows the display support arm 30 with the first, second and third swing arms 31, 32, 33 locked.

Turning back to FIG. 7, since the housing 20 and the first to third swing arms 31, 32, 33 are locked, the operator for example moves the ultrasonic imaging apparatus 10 (step S705). At this time, there is no fear of the display support arm 30 expanding and the position of the display 90 changing due to vibration caused by the movement or due to a sudden acceleration caused by direction changing.

Thereafter, in a new imaging site, the operator causes the rotary knob 36 lying on a side face of the first swing arm 31 to rotate and accommodates the hook 48 into the receptacle hole 35 to make the hook unlockable (step S706). In this unlockable state, the lock setting device 37 brings the hook 48 into such a state as shown in FIG. 4(B). In this state, the hook 48 is received within the receptacle hole 35 and is disengaged from the fitting portion 51. In synchronism with this motion the plunger 62 is raised vertically above the plunger hole 52 formed in the first end portion 41. Then, the locked state between the housing 20 and the first swing arm 31 by the first rod 63 is released.

Thereafter, the operator brings the display support arm 30 into a state best suited for performing imaging using the ultrasonic imaging apparatus 10 and picks up an image of the subject (step S707). For bringing the display support arm 30 into an optimal state for imaging, the first, second and third swing arms 31, 32, 33 are rotated to search for an optimal position. At this time, the operator's operation is performed easily without causing any inconvenience because the first, second and third lock devices are locked.

Particularly, the hook 48 is received within the receptacle hole 35 of the first swing arm 31, so when the first swing arm 31 is rotated, the operator's operation can be performed easily without collision with an external obstacle.

Thereafter, when the imaging operation is ended, the operator performs for example the steps S701 to S704 and brings the display 90 into a locked state at the home position, ready for movement.

In this embodiment, as described above, when the rotary knob 36 as a hook rotating device is rotated into the lockable state, the rod-like hook 48 is projected vertically above the first swing arm 31 and at the same time the plunger 62 is allowed to descend into the plunger hole 52, then an autolocking is established while the first swing arm 31 or the second swing arm 32 is rotated between the fitting portion 51 of the second swing arm 32 opposed thereto and the first rod hole 71 of the housing 20. Therefore, the lockable state is established by a single rotating motion of the rotary knob 36 and thereafter a lock is fastened automatically to an optimal position, e.g., home position, by rotating motions of the first and second swing arms 31, 32 and thus it is possible to effect locking easily without requiring much time and labor and fix the display 90.

Although in this embodiment the first, second and third swing arms 31, 32, 33 are locked in this order, the locking order of the first swing arm 31 is not limited to the order insofar as the third swing arm 33 is locked after locking the second swing arm 32. For example, the locking may be done in an order such that the second swing arm 32 is locked first, followed by locking of the first swing arm 31 and subsequent locking of the third swing arm 33. It is possible for the operator to select an appropriate order according to the situation and lock all of the first to third swing arms 31-33 efficiently.

Many widely different embodiments of the invention may be configured without departing from the spirit and the scope of the present invention. It should be understood that the present invention is not limited to the specific embodiments described in the specification, except as defined in the appended claims.

The invention claimed is:

1. A display support arm comprising:
   a first swing arm having a first end portion positioned vertically on top of a housing and further having a second end portion, the first swing arm causing the second end portion to rotate in a horizontal plane with the first end portion as a rotational center;
   a second swing arm having a third end portion joined vertically to the second end portion and further having a fourth end portion, the second swing arm causing the fourth end portion to rotate in a horizontal plane with the third end portion as a rotational center;
   a display joined vertically to the fourth end portion;
   a first lock device for locking a rotational motion of the first swing arm automatically when the housing and the first swing arm reach a predetermined relative position;
   a second lock device for locking a relative rotational motion of the first and second swing arms automatically when the first and second swing arms vertically reach a position where the first swing arm and the second swing arm overlap each other; and
   a lock setting device for switching the first and second lock devices in one behavior to a lockable state able to effect locking automatically in the predetermined relative position and the overlapping position or an unlockable state failing to perform the locking in the predetermined relative position and the overlapping position.

2. A display support arm according to claim 1, wherein the second swing arm and the display are provided vertically above the first swing arm.

3. A display support arm according to claim 1, wherein the first lock device comprises:
- a plunger hole extending vertically and formed in a joining surface of the first end portion for joining to the housing;
- a plunger disposed within the plunger hole and having a first rod movable vertically; and
- a first rod hole for insertion therein of the first rod, the first rod hole being formed in a joining surface of the housing confronting the joining surface of the first end portion.

4. A display support arm according to claim 1, wherein the second lock device comprises:
- a rod-like hook projecting vertically upwards from the first swing arm; and
- a fitting portion for fitting with an upper end of the rod-like hook, the fitting portion being formed on the surface of the second swing arm confronting the first swing arm.

5. A display support arm according to claim 4, wherein the lock setting device includes a hook rotating device for switching by rotation the rod-like hook mounted to the first swing arm to the projecting state as the lockable state or a state as the unlockable state in which the rod-like hook extends along an arm of the first swing arm.

6. A display support arm according to claim 5, wherein the hook rotating device includes a rotary knob for performing the rotation manually, the rotary knob being mounted to a side face of the first swing arm.

7. A display support arm according to claim 5, wherein the hook rotating device includes a resilient member for maintaining the projecting state and the extending-along-the-arm state with resilience.

8. A display support arm according to claim 5, wherein the hook rotating device includes a link device for bringing the plunger into a vertically raised state as the unlockable state; and a vertically lowered state as the lockable state, in synchronism with the switching operation.

9. A display support arm according to claim 4, wherein the fitting portion comprises:
- an opening in a direction along an arm of the second swing arm, the opening serving as an inlet of the fitting; and
- a guide surface formed around the opening and having an oblique inclination with respect to said direction.

10. A display support arm according to claim 9, wherein the guide surface is disposed on a circular path, the circular path being described by the projecting position of the rod-like hook present on the first swing arm when the first swing arm is rotated with the second end portion as a rotational center.

11. A display support arm according to claim 4, wherein the display includes a third swing arm having a fifth end portion joined to the fourth end portion vertically downward and further having a sixth end portion, the third swing arm causing the display positioned at the sixth end portion to rotate in a horizontal plane.

12. A display support arm according to claim 11, further comprising a third lock device for locking the rotational motion of the second swing arm and that of the third swing arm automatically when the lock setting device is in its lockable state and when the second and third swing arms perform a relative rotational motion and reach a predetermined relative position in case of the upper end portion of the hook and the fitting portion being fitted together.

13. A display support arm according to claim 12, wherein the third lock device includes a second rod and a second rod hole formed in a side face of the fifth end portion for insertion therein of the second rod, the second rod being disposed in the opening of the fitting portion and movable in a direction of the arm of the second swing arm while penetrating the fitting portion when the fitting portion is positioned near the side face of the fifth end portion.

14. A display support arm according to claim 11, wherein the third swing arm includes a rotating device for rotating the display around a horizontal rotary shaft orthogonal to a direction along an arm of the third swing arm.

15. A display support arm according to claim 12, wherein the third swing arm includes a rotating device for rotating the display around a horizontal rotary shaft orthogonal to a direction along an arm of the third swing arm.

16. A display support arm according to claim 13, wherein the third swing arm includes a rotating device for rotating the display around a horizontal rotary shaft orthogonal to a direction along an arm of the third swing arm.

17. An ultrasonic imaging apparatus comprising:
- a first swing arm having a first end portion positioned vertically on top of a housing and further having a second end portion, the first swing arm causing the second end portion to rotate in a horizontal plane with the first end portion as a rotational center;
- a second swing arm having a third end portion joined vertically to the second end portion and further having a fourth end portion, the second swing arm causing the fourth end portion to rotate in a horizontal plane with the third end portion as a rotational center;
- a display joined vertically to the fourth end portion;
- a first lock device for locking a rotational motion of the first swing arm automatically when the housing and the first swing arm reach a predetermined relative position;
- a second lock device for locking a relative rotational motion of the first and second swing arms automatically when the first and second swing arms vertically reach a position where the first swing arm and the second swing arm overlap each other; and
- a lock setting device for switching the first and second lock devices in one behavior to a lockable state able to effect locking automatically in the predetermined relative position and the overlapping position or an unlockable state failing to perform the locking in the predetermined relative position and the overlapping position.

18. An ultrasonic imaging apparatus according to claim 17, wherein the display includes a third swing arm having a fifth end portion joined to the fourth end portion vertically downward and further having a sixth end portion, the third swing arm causing the display positioned at the sixth end portion to rotate in a horizontal plane.

19. An ultrasonic imaging apparatus according to claim 18, further comprising a third lock device for locking the rotational motion of the second swing arm and that of the third swing arm automatically when the lock setting device is in its lockable state and when the second and third swing arms perform a relative rotational motion and reach a predetermined relative position in case of the second lock device being locked.

* * * * *